United States Patent [19]

Otoshi et al.

[11] Patent Number: 4,822,498

[45] Date of Patent: Apr. 18, 1989

[54] FIRE-EXTINGUISHING COMPOSITION

[75] Inventors: Sachio Otoshi, Yokohama; Hideaki Hatayama, late of Tokyo, both of Japan, by Seiichi Hatayama, legal representative

[73] Assignee: Asahi Glass Company Ltd., Tokyo, Japan

[21] Appl. No.: 81,729

[22] Filed: Aug. 5, 1987

[30] Foreign Application Priority Data

Aug. 6, 1986 [DE] Fed. Rep. of Germany .... 61-183337

[51] Int. Cl.$^4$ .......................... A62D 1/00; A62C 1/12
[52] U.S. Cl. .......................................... 252/2; 169/46; 169/47; 252/3; 252/8.05; 252/351
[58] Field of Search ............ 252/3, 8.05, 6.5, DIG. 7, 252/351, 354, 356; 169/45, 46, 47; 422/42

[56] References Cited

U.S. PATENT DOCUMENTS

| | | | |
|---|---|---|---|
| 4,038,195 | 11/1974 | Chiesa, Jr. | 252/3 |
| 4,042,522 | 8/1977 | Falk | 252/8.05 |
| 4,090,967 | 5/1978 | Falk | 252/8.05 |
| 4,099,574 | 7/1978 | Cooper et al. | 169/47 |
| 4,209,407 | 6/1980 | Schuierer et al. | 169/47 |
| 4,278,552 | 1/1981 | Hisamoto et al. | 252/3 |
| 4,359,096 | 11/1982 | Berger | 252/3 |
| 4,420,434 | 12/1983 | Falk | 252/3 |
| 4,536,298 | 8/1985 | Kamei et al. | 252/8.05 |
| 4,563,287 | 1/1986 | Hisamoto et al. | 252/2 |
| 4,594,167 | 6/1986 | Kobayashi et al. | 252/3 |

FOREIGN PATENT DOCUMENTS

| | | |
|---|---|---|
| 0002004 | 5/1979 | European Pat. Off. |
| 0039058 | 11/1981 | European Pat. Off. |
| 54-38838 | 11/1979 | Japan |

OTHER PUBLICATIONS

Chemical Abstracts, vol. 84, No. 4, Jan. 26th, 1976, p. 175, Abstract No. 19911d, Columbus, Ohio, U.S.; and JP-A-75 82 897 (Asahi Electro-Chemical Co., Ltd) 04-07-1975.

*Primary Examiner*—Howard J. Locker
*Attorney, Agent, or Firm*—Oblon, Fisher, Spivak, McClelland & Maier

[57] ABSTRACT

A fire-extinguishing composition comprising a fluorine-containing surfactant of the formula:

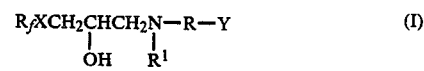

wherein $R_f$ is a polyfluoroalkyl group having from 3 to 20 carbon atoms, X is a bivalent connecting group containing an ether-type oxygen atom, R is an alkylene group, Y is

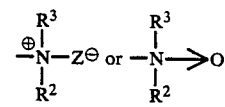

wherein $Z^\ominus$ is an anionic group-containing alkyl group, $R^1$ is a hydrogen atom, an alkyl group or a hydroxyalkyl group, or forms together with $R^2$ an alkylene group, $R^2$ is a hydrogen atom, an alkyl group or a hydroxyalkyl group, or forms together with $R^1$ an alkylene group, and $R^3$ is a hydrogen atom, an alkyl group or a hydroxyalkyl group.

5 Claims, No Drawings

FIRE-EXTINGUISHING COMPOSITION

The present invention relates to a fire-extinguishing composition. More particularly, it relates to a fire-extinguishing composition useful particularly for extinguishing fire of a polar solvent.

A number of foaming fire-extinguishing compositions wherein a fluorine-containing surfactant is used, have been known. However, these fire-extinguishing compositions tend to undergo defoaming when applied to a polar solvent, and they are incapable of effectively extinguishing the fire of a polar solvent. Under the circumstances, it has been proposed to add a fluorine-containing surfactant to a protein foam so that the protein will be effective for extinguishing fire of a polar solvent, e.g. in Japanese Examined Patent Publication No. 38838/1979 or U.S. Pat. No. 4,278,552. However, such fluorine-containing surfactants are not necessarily effective, and there have been problems such that precipitates are likely to generate when they are mixed with a protein, and the storage stability is poor. Furthermore, no adequate fire-extinguishing properties are obtainable even if a conventional fluorine-containing surfactant is incorporated. Although it may be used in a 3% concentration (diluted 33 times with water) as a fire-extinguisher for oil flame, a high concentration as high as a 6% concentration (diluted 16.7 times with water) is required to provide adequate fire-extinguishing performance as a fire-extinguisher for polar solvent flame. Thus, the mixing ratio with water or sea water has to be changed depending upon the type of the flame to be extinguished.

The present inventors have conducted extensive research with an aim to solve the above-mentioned problems, and have found an interesting fact that by using, as a fluorine-containing surfactant in a fire-extinguishing composition, a compound containing both an ether-type oxygen atom and a hydroxyl group and being weakly cationic, i.e. a compound having a specific chemical structure which has not been known before, it is possible to obtain a fire-extinguishing composition which does not undergo defoaming even when applied to a polar solvent, and which does not form precipitates even when mixed with a protein. The present invention has been accomplished on the basis of this discovery.

The present invention provides a fire-extinguishing composition comprising 100 parts by weight of water and from 0.02 to 5.0 parts by weight of a fluorine-containing surfactant of the formula:

$$R_f XCH_2CHCH_2N-R-Y \quad (I)$$
$$\quad\quad\quad | \quad\quad |$$
$$\quad\quad\quad OH \quad R^1$$

wherein $R_f$ is a polyfluoroalkyl group having from 3 to 20 carbon atoms, X is a bivalent connecting group containing an ether-type oxygen atom, R is an alkylene group, Y is $$\begin{array}{cc} R^3 & R^3 \\ | & | \\ -\overset{\oplus}{N}-Z^{\ominus} \text{ or } & -N \longrightarrow O, \\ | & | \\ R^2 & R^2 \end{array}$$

wherein $Z^{\ominus}$ is an anionic group-containing alkyl group, $R^1$ is a hydrogen atom, an alkyl group or a hydroxyalkyl group, or forms together with $R^2$ an alkylene group, $R^2$ is a hydrogen atom, an alkyl group or a hydroxyalkyl group, or forms together with $R^1$ an alkylene group, and $R^3$ is a hydrogen atom, an alkyl group or a hydroxyalkyl group.

Now, the present invention will be described in detail with reference to the preferred embodiments.

In the present invention, $R_f$ is preferably a straight chain or branched chain perfluoroalkyl group having from 3 to 20 carbon atoms, but it may be a polyfluoroalkyl group wherein some of fluorine atoms may be substituted by hydrogen atoms or chlorine atoms. Further, $R_f$ includes a branched chain polyfluoroalkyl group obtained by oligomerization of $CF_2=CF_2$ or $CF_3CF=CF_2$, and $$C_3F_7O-(C_3F_6O)_{\overline{h}}\overset{O}{\underset{||}{C}}-$$

wherein h is an integer of from 0 to 5.

X is a bivalent connecting group containing an ether type oxygen atom, and may be represented by the formula $-R^4-O-(C_nH_{2n}O)_{\overline{k}}$, or $-Q-(C_nH_{2n}O)_{\overline{l}}$, wherein Q is $$\begin{array}{ccccc} -CON-, & -SO_2N-, & -N-, & \text{or} & -N-R^7-N-, \\ | & | & | & & | \quad\quad\quad | \\ R^5 & R^5 & R^5 & & R^5 \quad\quad R^6 \end{array}$$

wherein each of $R^4$ and $R^7$ is an alkylene group having from 1 to 10 carbon atoms, n is an integer of from 2 to 4, k is an integer of from 0 to 10, l is an integer of from 1 to 10, and each of $R^5$ and $R^6$ is a hydrogen atom or an alkyl group.

In the formula I, R is an alkylene group having from 1 to 10 carbon atoms.

Y is $$\begin{array}{cc} R^3 & R^3 \\ | & | \\ -\overset{\oplus}{N}-Z^{\ominus} \text{ or } & -N \longrightarrow O, \\ | & | \\ R^2 & R^2 \end{array}$$

wherein $Z^{\ominus}$ is an anionic group-containing alkyl group.

$R^1$ is a hydrogen atom, an alkyl group or a hydroxyalkyl group, or it forms together with $R^2$ an alkylene group.

$R^2$ is a hydrogen atom, an alkyl group or a hydroxyalkyl group, or it forms together with $R^1$ an alkylene group.

$R^3$ is a hydrogen atom, an alkyl group or a hydroxyalkyl group.

As a specific example of $Z^{\ominus}$, $-(CH_2)_{\overline{m}}COO^{\ominus}$ or $-(CH_2)_{\overline{m}}SO_3^{\ominus}$ wherein m is an integer of from 1 to 5, may be mentioned.

Specifically, the following compounds are preferred.

$$C_8F_{17}C_2H_4OCH_2CHCH_2NH(CH_2)_3\overset{\oplus}{N}(CH_3)_2$$
$$\quad\quad\quad\quad\quad\quad\quad | \quad\quad\quad\quad\quad\quad\quad\quad |$$
$$\quad\quad\quad\quad\quad\quad\quad OH \quad\quad\quad\quad\quad\quad\quad\quad CH_2COO^{\ominus}$$

$$C_8F_{17}C_2H_4OCH_2CHCH_2NH(CH_2)_3N(CH_3)_2$$
$$\quad\quad\quad\quad\quad\quad\quad | \quad\quad\quad\quad\quad\quad\quad\quad\quad \downarrow$$
$$\quad\quad\quad\quad\quad\quad\quad OH \quad\quad\quad\quad\quad\quad\quad\quad\quad O$$

-continued $$C_6F_{13}C_2H_4OC_2H_4OCH_2\underset{OH}{CHCH_2}NH(CH_2)_3\overset{\oplus}{N}(CH_3)_2$$
$$\phantom{xxxxxxxxxxxxxxxxxxxxxxxxx}CH_2COO^{\ominus}$$

$$C_{10}F_{21}CH_2OC_3H_6OCH_2\underset{OH}{CHCH_2}NH(CH_2)_3\overset{\oplus}{N}(CH_3).C_2H_4OH$$
$$\phantom{xxxxxxxxxxxxxxxxxxxxxxxxx}CH_2COO^{\ominus}$$

$$C_8F_{17}CONHC_2H_4OCH_2\underset{OH}{CHCH_2}NH(CH_2)_3\overset{\oplus}{N}(CH_3)_2$$
$$\phantom{xxxxxxxxxxxxxxxxxxxxxxxxx}C_3H_6SO_3^{\ominus}$$

$$C_6F_{13}SO_2\underset{C_2H_5}{N}C_2H_4OCH_2\underset{OH}{CHCH_2}NH(CH_2)_3N(CH_3).C_2H_4OH$$

$$C_{10}F_{21}NHC_2H_4OCH_2\underset{OH}{CHCH_2}NH(CH_2)_3\overset{\oplus}{N}(CH_3)_2$$
$$\phantom{xxxxxxxxxxxxxxxxxxxxxxxxx}CH_2COO^{\ominus}$$

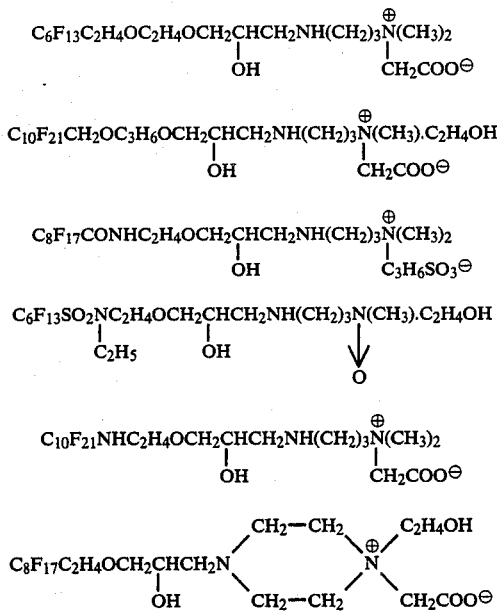

The fire-extinguishing composition of the present invention contains the above-mentioned specific fluorine-containing surfactant in water. When used as a fire-extinguisher for a flammble liquid, it may be used in combination with various hydrocarbon surfactants for the purpose of improving the foaming properties or reducing the surface tension. For example, by the combination with a hydrocarbon amphoteric surfactant having excellent foaming properties or with a hydrocarbon nonionic surfactant having excellent surface tension-reducing properties, it is possible to improve the spreading time, sealing properties or foaming rate as a fire-extinguisher. When used as a fluoroprotein foaming fire-extinguisher, it may be used in combination with an assistant foaming agent such as a partially hydrolyzed protein, a foam stabilizer such as a polyoxyethylene glycol or an alkylether of an alkylene glycol, an antifreeze such as glycerol, ethylene glycol or propylene glycol, a silicone surfactant, or various additives such as a pH controlling agent or rust-preventing agent.

In the present invention, the proportion of the fluorine-containing surfactant to water may be as low as from 0.002 to 5.0 parts by weight, preferably from 0.005 to 0.2 part by weight, relative to 100 parts by weight of water, when it is used as diluted with water, whereby an adequate performance can be obtained. The fire-extinguishing composition of the present invention can be used in a wide range of concentration without foaming precipitates as a protein foaming fire-extinguisher, as a water-film foaming type fire-extinguisher or as an interface foaming fire-extinguisher against the flame of a flammable liquid such as gasoline, kerosine oil, heavy oil, cyclohexane, thinner, benzene or toluene. Further, it is effectively useful without defoaming against the flame of a polar solvent such as an alcohol or acetone.

In the present invention, the fluorine-containing surfactant is weakly cationic, and it is believed that when reacted with an anionic protein, it becomes insoluble in a polar solvent, whereby it does not undergo defoaming when applied to a polar solvent. Whereas, in the case of conventional fluorine-containing surfactants, the solubility in water tends to be low, whereby precipitation is likely to generate. The surfactant of the present invention contains both a hydroxyl group and an ether group in its molecule, whereby the hydrophilic properties will not be lowered, and no precipitation takes place.

Now, the present invention will be described in further detail with reference to Examples. However, it should be understood that the present invention is by no means restricted by such specific Examples.

PREPARATION EXAMPLES

Into a 500cc three-necked flask, 100 g of $C_8F_{17}C_2H_4OH$, 40 g of

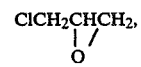

100g of 1,1,2-trifluoro-1,2,2-trichloroethane and 17 g of NaOH were introduced and reacted at 46° C. for 10 hours to obtain

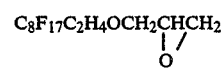

at a conversion of 100%. The product was washed with water to remove NaCl, NaOH and

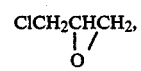

whereby $C_8F_{17}C_2H_4OCH_2CHCH_2$ was obtained in a yield of 90%.

Then, 50 g of

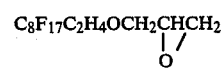

and 98 g of $NH_2(CH_2)_3N(CH_3)_2$ were introduced into a similar three-necked flask, and reacted at 60° C. for two hours by using 100 g of ethanol as a solvent to obtain $$C_8F_{17}C_2H_4OCH_2\underset{OH}{CHCH_2}NH(CH_2)_3N(CH_3)_2,$$

whereupon ethanol as the solvent and unreacted $NH_2(CH_2)_3N(CH_3)_2$ were removed by a rotary evaporator. Then, 100 g of the above reaction product, 100 g of IPA (isopropyl alcohol), 23 g of $ClCH_2COOH$ and 24 g of an aqueous solution containing 40% of NaOH were introduced into a three-necked flask and reacted at 83° C. for 5 hours to obtain desired

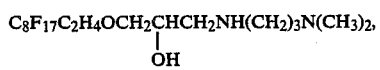

In the same manner as above, various surfactants as shown in the following Table were prepared.

| Surfactants |
| --- |
| 1    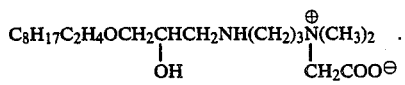 |

Surfactants (continued)

2. $C_6F_{13}CH_2OCH_2\underset{OH}{CHCH_2}NH(CH_2)_3\overset{\oplus}{N}(CH_3)C_2H_4OH$
   $\phantom{C_6F_{13}CH_2OCH_2CHCH_2NH(CH_2)_3N(CH_3)}CH_2COO^{\ominus}$ 3. $C_{10}F_{21}C_2H_4OCH_2\underset{OH}{CHCH_2}NH(CH_2)_3\overset{\oplus}{N}(CH_3)_2$
   $\phantom{C_{10}F_{21}C_2H_4OCH_2CHCH_2NH(CH_2)_3N(CH_3)_2}C_3H_6SO_3^{\ominus}$ 4. $C_8F_{17}CONHC_2H_4OCH_2\underset{OH}{CHCH_2}NH(CH_2)_3N(CH_3)_2$
   $\phantom{xxxxxxxxxxxxxxxxxxxxxxxxxxxxxxxxxxxxx}\downarrow O$ 5. $C_6F_{13}CONHC_2H_4OCH_2\underset{OH}{CHCH_2}NH(CH_2)_3\overset{\oplus}{N}(CH_3)_2$
   $\phantom{C_6F_{13}CONHC_2H_4OCH_2CHCH_2NH(CH_2)_3N(CH_3)_2}CH_2COO^{\ominus}$ 6. $C_{10}F_{21}C_2H_4OCH_2\underset{OH}{CHCH_2}N\begin{array}{c}CH_2CH_2\\ \diagdown\end{array}\overset{\oplus}{N}\begin{array}{c}C_2H_4OH\\ \diagup \\ \diagdown CH_2COO^{\ominus}\end{array}$
   $\phantom{xxxxxxxxxxxxxxxxxxxxxxxx}CH_2CH_2$

WORKING EXAMPLES

Fire-extinguishing tests were conducted in the following manner by using fire-extinguisher solutions prepared by adding 1% by weight of the above-identified fluorine-containing surfactants, respectively, to protein foaming solutions.

Fuel: 200 liters of isopropylalcohol in a tank of 1 m × 2 m × 0.5 m.
Preburning time: one minute
Supply of the fire-extinguisher: 10 liter/min
Foaming nozzle: standard products as stipulated in Ordinance No. 26 of the Municipal Ministry of Japan
Foam expansion rate: rate as stipulated in Ordinance No. 26 of the Minicipal Ministry of Japan
25% drainage time: method as stipulated in Ordinance No. 26 of the Municipal Ministry of Japan
The fire-extinguisher solution was used as diluted 33 times with water (3% concentration).
Amount of precipitates: the fire-extinguisher solution was stored at 65° C. for 72 hours and centrifuged at 3,000 rpm, whereupon the precipitates were measured by volume %.

Results of fire-extinguishing test

| Surfactant | Foam expansion | 25% drainage time | Extinguish time | Precipitates (vol %) |
|---|---|---|---|---|
| Example 1 | 7.6 | 5'02" | 5'04" | 0.15 |
| Example 2 | 7.1 | 5'13" | 4'36" | " |
| Example 3 | 7.8 | 5'05" | 4'48" | " |
| Example 4 | 7.3 | 4'52" | 4'28" | " |
| Example 5 | 7.3 | 4'48" | 4'57" | " |
| Example 6 | 7.4 | 4'56" | 4'50" | " |
| Comparative Examples | | | | |
| Not added | 7.0 | 4'30" | Not extinguished | " |
| $C_8F_{17}COONH_4$ | 6.2 | 3'10" | " | " |
| $C_8F_{17}SO_2\underset{C_2H_5}{N}(CH_2)_3\overset{\oplus}{N}$ 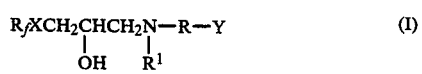 —$(CH_3)_3Br^{\ominus}$ | 5.8 | 3'08" | " | 0.6 |
| $C_{10}F_{21}CONH(CH_2)_3$ 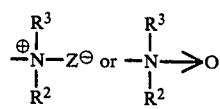 —$\overset{\oplus}{N}(CH_3)_2$ $\phantom{xx}CH_2COO^{\ominus}$ | 5.9 | 3'25" | " | 0.5 |
| | 5.9 | 3'25" | " | 0.5 |
| $C_8F_{17}CH_2\underset{OH}{CHCH_2}$ —$\overset{\oplus}{NH}(CH_2)_3\overset{}{N}(CH_3)_2$ $\phantom{xx}CH_2COO^{\ominus}$ | 5.2 | 3'00" | 5'30" | 0.6 |

The fire-extinguishing composition of the present invention exhibits excellent fire-extinguishing performance particularly when applied to the fire of a polar solvent. It exhibits adequate fire-extinguishing performance even in the form diluted 33 times with water. Further, the fire-extinguisher solution has excellent storage stability without forming precipitates, and it is free from such a problem that the fire-extinguishing performance deteriorates. The fire-extinguishing composition of the present invention is also effective as a general purpose fire-extinguisher for oil flame or as a water-film forming fire-extinguisher, although it is particularly effective for extinguishing the fire of a polar solvent.

We claim:

1. An aqueous fire-extinguishing composition comprising a fluorine-containing surfactant of the formula:

$$R_f XCH_2\underset{OH}{CHCH_2}\underset{R^1}{N}-R-Y \quad (I)$$

wherein $R_f$ is a polyfluoroalkyl group having from 3 to 20 carbon atoms, X is a bivalent connecting group containing an ether-type oxygen atom, R is an alkylene group, Y is $$\overset{\oplus}{\underset{R^2}{\overset{R^3}{N}}}-Z^{\ominus} \text{ or } \underset{R^2}{\overset{R^3}{N}}\rightarrow O$$

wherein $Z^{\ominus}$ is an anionic group-containing alkyl group, $R^1$ is a hydrogen atom, an alkyl group or a hydroxyalkyl group, or forms together with $R^2$ an alkylene group, $R^2$ is a hydrogen atom, an alkyl group or a hydroxyalkyl group, or forms together with $R^1$ an alkylene group, and $R^3$ is a hydrogen atom, an alkyl group or a hydroxyalkyl group.

2. The fire-extinguishing composition according to claim 1, wherein $R_f$ is a perfluoroalkyl group having from 6 to 12 carbon atoms, $R^1$ is a hydrogen atom, and each of $R^2$ and $R^3$ is a methyl group.

3. The fire-extinguishing composition according to claim 1, which is useful for extinguishing fire of a polar solvent.

4. The fire-extinguishing composition according to claim 1, wherein the surfactant of the formula I is in an amount of from 0.002 to 5.0 part by weight relative to 100 parts by weight of water.

5. A method for extinguishing a fire, which comprises applying to the fire a fire-extinguishing composition comprising a fluorine-containing surfactant of the formula:

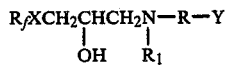   (I)

wherein $R_f$ is a polyfluoroalkyl group having from 3 to 20 carbon atoms, X is a bivalent connecting group containing an ether-type oxygen atom, R is an alkylene group, Y is

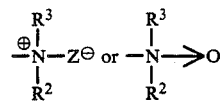

wherein $Z^\ominus$ is an anionic group-containing alkyl group, $R^1$ is a hydrogen atom, an alkyl group or a hydroxyalkyl group, or forms together with $R^2$ an alkylene group, $R^2$ is a hydrogen atom, an alkyl group or a hydroxyalkyl group, or forms together with $R^1$ an alkylene group, and $R^3$ is a hydrogen atom, an alkyl group or a hydroxyalkyl group.

* * * * *